United States Patent
Godsmark et al.

(10) Patent No.: US 9,168,518 B2
(45) Date of Patent: Oct. 27, 2015

(54) REGENERATION OF OLIGOMERISATION CATALYSTS AND THEIR USE

(75) Inventors: John Stephen Godsmark, Antwerp (GB); Georges Marie Karel Mathys, Bierbeek (BE); Hans Karel Theresia Goris, Zaventem (BE); Roger Eijkhoudt, Huijbergen (NL); Stephen Harold Brown, Annandale, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 371 days.

(21) Appl. No.: 13/637,404

(22) PCT Filed: Apr. 28, 2010

(86) PCT No.: PCT/US2010/032805
§ 371 (c)(1),
(2), (4) Date: Nov. 26, 2012

(87) PCT Pub. No.: WO2011/136765
PCT Pub. Date: Nov. 3, 2011

(65) Prior Publication Data
US 2013/0204060 A1    Aug. 8, 2013

(51) Int. Cl.
*B01J 38/12* (2006.01)
*B01J 29/90* (2006.01)
*B01J 29/70* (2006.01)
*B01J 29/80* (2006.01)
*B01J 38/02* (2006.01)
*B01J 38/26* (2006.01)
*B01J 38/28* (2006.01)
*C07C 2/12* (2006.01)

(52) U.S. Cl.
CPC .............. *B01J 29/90* (2013.01); *B01J 29/7026* (2013.01); *B01J 29/7042* (2013.01); *B01J 29/80* (2013.01); *B01J 38/02* (2013.01); *B01J 38/12* (2013.01); *B01J 38/26* (2013.01); *B01J 38/28* (2013.01); *C07C 2/12* (2013.01)

(58) Field of Classification Search
CPC ........................................................ B01J 38/12
USPC ........................................................... 502/38
See application file for complete search history.

(56) References Cited

U.S. PATENT DOCUMENTS

| 3,069,362 A | 12/1962 | Mays et al. |
| 4,560,536 A | 12/1985 | Tabak |
| 5,043,517 A * | 8/1991 | Haddad et al. ................ 585/533 |
| 5,756,414 A | 5/1998 | Huang et al. |

FOREIGN PATENT DOCUMENTS

| EP | 0 426 400 | 5/1991 |
| EP | 0 604 689 | 7/1994 |
| WO | WO 98/55228 | 12/1998 |
| WO | WO 2004/080591 | 9/2004 |
| WO | WO 2006/133967 | 12/2006 |
| WO | WO 2009/058522 | 5/2009 |

* cited by examiner

*Primary Examiner* — Edward Johnson
(74) *Attorney, Agent, or Firm* — Leandroo Arechederra, III; Luke A. Parsons

(57) ABSTRACT

Deactivation of a zeolite catalyst during its use to catalyse the oligomerisation of olefins, is often believed to be a result of the formation of high boiling polymers as by-products. These by-products can remain on the catalyst and undergo further conversion to higher molecular weight polymers, which resemble heavy tars and in some cases even have the appearance of coke-like material. These materials can coat the catalyst particles and plug pores in the catalyst, thereby causing catalyst deactivation. The invention relates to an improved method for regenerating such a catalyst.

5 Claims, No Drawings

US 9,168,518 B2

REGENERATION OF OLIGOMERISATION CATALYSTS AND THEIR USE

PRIORITY CLAIM

This application is a National Stage Application of International Application No. PCT/US2010/032805 filed Apr. 28, 2010, the disclosure of which is fully incorporated herein by reference.

FIELD OF THE INVENTION

The present invention relates to zeolite catalysts that are useful for olefin oligomerisation and is particularly concerned with the regeneration of such catalysts.

BACKGROUND OF THE INVENTION

Extending the life of the catalysts that are used for olefin oligomerisation, particularly, oligomerisation of $C_3$ to $C_6$ olefins, particularly, $C_3$ and $C_4$ olefins, in order to produce $C_8$ and $C_{10}$ olefins is highly desirable. The oligomerisation product may further be hydroformylated and hydrogenated to produce alcohols. $C_9$, $C_{10}$ and $C_{12}$ alcohols are useful in many areas one of which is in esterification to produce plasticizer esters such as phthalates, sebaccates, cyclohexanoates, pyromellitates, and adipates. These materials are used to plasticise plastics such as polyvinyl chloride (PVC).

In all these oligomerisation processes regardless of the length of the run, the zeolite catalyst becomes deactivated over time usually due to the formation of deposits of carbon (known as coke) in the pores of the zeolite. This leads to a reduction in conversion of olefins to oligomers and a reduction in the selectivity of the conversion.

The H zeolites, e.g., ZSM-22 and ZSM-57, are preferred catalysts for the oligomerisation of olefins in that they have a pore structure which enables the production of olefin oligomers, particularly, octenes and nonenes having a structure suitable for hydroformylation to produce alcohols for plasticizer production. These catalysts are particularly prone to coke formation and thus require regeneration; however, they are also easily damaged under typical regeneration conditions.

There is therefore a need to optimise the regeneration of such catalysts in order to extend their life in the oligomerisation of olefins to produce feedstocks for hydroformylation to produce alcohols useful in the manufacture of plasticisers.

The coke that forms on these catalysts when they are used for olefin oligomerisation takes different forms and can be made up of light coke, heavy coke, and hard coke. Traditionally, coke is removed from catalysts by burning. However, the pore structure of ZSM-22 and ZSM-57 catalysts are susceptible to damage at the elevated temperatures that have traditionally been required to remove all the coke. For example, it has been necessary to remove hard coke from ZSM-22 by heating to temperatures around 600° C. which has been found to damage the zeolite structure. Damage to the structure starts to occur at about 510° C. and reduces the catalyst activity and selectivity in converting olefins to oligomers.

It has now been found that by control of the heating cycle and the amount of water present during the catalyst regeneration a substantial amount of the hard coke can be removed while reducing the amount of damage caused to the pore structure of the zeolite. It has also been found that it can be beneficial to retain a small amount of coke on the regenerated catalyst as a totally clean regenerated catalyst can be too delicate for subsequent oligomerisation operations.

SUMMARY OF THE INVENTION

The invention provides a process for the regeneration of a catalyst selected from ZSM-22; ZSM-57; or mixtures thereof which catalyst has been used for the oligomerisation of olefins comprising the following steps:
  i) heating the catalyst to a temperature in the range 300° C. to 450° C. under an inert dry atmosphere; and
  ii) heating the catalyst to a temperature in the range of 450° C. to 500° C. in a dry oxygen containing atmosphere.

DETAILED DESCRIPTION OF THE INVENTION

We have found that the regeneration of a catalyst that has been used for olefin oligomerisation under these conditions can produce a regenerated catalyst with retained pore structure and having a residual carbon content of from 0.25 to 1.25 wt %, preferably 0.3 to 1.0 wt %, and which can be used for extended periods of olefin oligomerisation with retained conversion and selectivity. We have found this to be particularly useful in the production of olefins as feedstock for hydroformylation to produce plasticiser alcohols.

The length of time for which the catalyst is heated in the two steps of the regeneration process is important. However, the optimum time will depend upon the volume of the catalyst that is to be regenerated and also on the detailed design of the regeneration reactor. We prefer however that the total time for regeneration be no more than 100 hours and we have found that the second step can conveniently be performed in less than 68 hours, typically less than 50 hours.

The inert atmosphere employed in the first step of the regeneration process of the present invention is preferably a nitrogen atmosphere although other inert atmospheres may be used. The dry oxygen containing atmosphere employed in the second step may contain some moisture and some water will be present due to the water created during the burning of the carbon. We have found however that dry air, that is, air having a dew point below −10° C. is particularly suitable.

We have found that employing the regeneration techniques of the present invention together with the olefin oligomerisation techniques such as those described in PCT Publication No. WO 2008/074511 can lead to extended oligomerisation runs based on a catalyst which may be regenerated several times without a significant loss in activity or selectivity.

In a further embodiment, the invention provides for a continuous process for the oligomerisation of olefins employing a zeolite catalyst that has been regenerated according to the present invention. In particular, it provides such a process wherein an olefin containing hydrocarbon feed is passed over a bed of the regenerated zeolite catalyst in a tubular reactor wherein the life of the catalyst on stream is extended by cooling the shell side of the reactor by a temperature control fluid and the temperature of the reaction is monitored and the space velocity of the olefin stream fed to the reactor is adjusted according to the temperature measured. The combination of the catalyst regeneration and the extended overall catalyst life due to the cooling provides significantly extended catalyst life.

By this cooling process, within a desired average reaction temperature required for a target conversion, the axial temperature profile in the reactor tube is flattened in the early part of the run, and is again sharpened in the last part of the run, both effects contributing to a more gradual catalyst deactivation and a longer overall catalyst life.

This technique coupled with regeneration according to the present invention gives extended catalyst life.

As is described in PCT Publication No. WO 2008/074511 at the beginning of an oligomerisation run, when the catalyst is fresh or freshly regenerated and is having a high activity, the temperature profile along the reactor tube typically shows a sharp peak, with the peak temperature occurring close to the inlet of the reactor. We have found that it is beneficial to operate at the start of run with a relatively high space velocity, i.e., with a space velocity that is above the average over the entire run, because, for the same average reaction temperature, the temperature profile is flatter and the peak temperature is lowered relative to the (average) temperature of the reaction. This reduces the catalyst deactivation rate around the location of the peak temperature and thereby contributes to a longer reactor runlength.

In the typical operation of a tubular reactor with a temperature control fluid on the shell side of the reactor, a temperature profile will be observed over the length of a reactor tube. Conventionally, such operation is performed with the tubular reactor arranged such that the feed inlet is at the top and the reaction product outlet is at the bottom. The following description addresses such an arrangement, but it will be understood that the description applies equally to reactors not in top to bottom arrangement. Typically, the temperature profile initially increases at the inlet of the tube, when reaction heat is generated faster than it can be removed by the temperature control fluid around the tube. As the reactants convert further as they move along the tube and their concentration reduces, the reaction rate reduces and the rate of heat generation reduces. At the same time, the temperature in the tube increases, and the heat removal rate through the tube wall increases.

In the tubular processes the temperature increase at the initial part (e.g., top) of the tube can be sharp, and the temperature profile can show a sharp peak. The catalyst at the initial part (top) of the tube performs most of the reaction. Coke will build up where the temperature is at its highest which will deactivate the catalyst in that part of the tube and will then reduce the reactivity due to the catalyst deactivation, and the rate of heat generation will reduce, and hence the slope of the temperature increase in that part of the temperature profile will decline. The catalyst further along (down) the tube will then see a higher concentration of unreacted reactants and the reaction rate and, hence, heat generation rate will increase in that part of the tube. In this way, the peak in the temperature profile, known as "the peak temperature", will move along (down) the tube. In order to compensate for the reduced overall catalyst activity, heat removal is typically reduced by increasing the temperature of the temperature control fluid around the tube. The average temperature in the reactor and the temperature at the outlet of the tube or reactor will thereby be increased as the run progresses. In addition, the temperature of the feed delivered to the tube inlet may be adapted as well. Typically, it may be increased to keep as much of the reaction as possible at as early (high) as possible a location in the catalyst bed inside the tube. Any peak in the temperature profile therefore may not only move along (down) the tube as a production run proceeds but it may also become less sharp and less pronounced. These techniques are used to extend the catalyst life on stream and can be beneficially combined with regenerating the catalyst.

Embodiments of the invention further provide a continuous process for oligomerising an olefin comprising contacting the olefin with a zeolite catalyst regenerated in a reactor tube of a tubular reactor having a shell that contains a temperature control fluid for removing heat of reaction from the reactor tube, in which process the olefin containing hydrocarbon feed to the reactor contains at least 40 wt % of olefin and less than 30 ppm of water based on total hydrocarbon in the feed, wherein operating conditions are controlled such that the reaction product mixture exiting the reactor is at a pressure of at least 55 barg and wherein the shell side temperature control fluid parameters are controlled such that the peak temperature in the reactor tube is no more than 50° C. above the temperature of the temperature control fluid as said fluid exits the reactor, and wherein the reaction temperature is monitored and the space velocity of the feed is varied according to the reaction temperature.

In particular, the peak temperature may be controlled to be no more than 40° C., preferably no more than 30° C., particularly preferably, no more than 20° C., and most preferably no more than 10° C. above the temperature of the temperature control fluid as the temperature control fluid exits the reactor.

Where several tubular reactors are employed, it is preferred to provide separate preheaters for each of the reactors, so that the feed-temperature can be adjusted according to the temperature conditions within the specific reactor. The employment of one or more of these conditions together with low water level and the adjustment of the space velocity of the feed has been found to result in a significant improvement in catalyst life.

Feeds of single olefins and mixtures of olefins can be processed in tubular reactors employing a zeolite catalyst regenerated over extended runs, for example, up to at least 300 days continuous operation without undesirable loss of activity of the regenerated catalyst. We have found that regenerated catalyst life in excess of 1500 tonnes of oligomer per tonne of catalyst may be achieved and catalyst life as high as 10,000 tonnes of oligomer per tonne of catalyst, even as high as 18,000 tonnes or higher can be achieved.

The feed streams containing olefins such as $C_3$ and $C_4$ olefins are generally streams derived from steam cracking or catalytic cracking and the composition of the stream will depend upon the raw material from which it is produced and the production technology employed.

The maximum concentration of olefin in the feed that can be processed will depend upon the nature of the olefin or mixture of olefins that are to be oligomerised. However, we have found that propylene containing feeds that contain, e.g., up to 65 wt % propylene, more typically, up to 60 wt % propylene, most typically, up to 55 wt % propylene can be employed. Similarly we have found that butene containing feeds that contain, e.g., up to 80 wt % butene, such as, up to 70 wt % butene, typically, up to 65 wt % butene, most typically, up to 60 wt % butene can be processed. Similar amounts can be processed when mixed $C_3/C_4$ feeds are employed. The minimum amount of olefin in the feed is preferably 40 wt %. In the case where the feed contains propylene, the more preferred minimum is 44 wt %, yet more preferably 46 wt % and most preferably 48 wt %. In the case where a butenes feed is employed, the more preferred minimum is 46 wt %, yet more preferably, 50 wt %, such as at least 55 wt %, and most preferably at least 60 wt %.

Where peak temperature is controlled for satisfactory performance of the oligomerisation of olefins, for example $C_3$ to $C_6$ olefins, over a zeolite catalyst, the peak temperature in a tubular reactor may be measured by inserting a multipoint thermocouple in at least one of the reactor tubes. Spider-shaped inserts may be used to keep the thermocouple in the centre of the tube. It is preferred that the thermocouple can detect the temperature at various locations along a significant portion of the length of the tube, preferably, towards the inlet end of the tube. Desirably, temperature is measured over at least the first 50%, or possibly 75% of the length of the tube from the inlet end, and at a plurality of points. For example, it is preferred to make measurements at from 10 to 20 points, such as 15 points, in a tube that is 3 to 10 meters (approx 10 to 33 feet) in length. The parameters of the temperature control fluid contained within the tubular reactor, for example the temperature and/or the flow rate, may then be adjusted in response to the temperature measured by the thermocouples, in order to maintain the peak temperature in the tube within the desired range according to the temperature control fluid outlet temperature. By appropriate adjustment of the parameters, this enables the process fluid temperature to be maintained at optimum conditions.

Where the reactor consists of a number of parallel tubes, a multitude of those tubes may be provided with a multipoint thermocouple, although this is not essential.

The temperature of a tubular reactor is controlled by passing a temperature control fluid around the shell side of the reactor tubes. In a preferred embodiment, the tubular reactor consists of several tubes mounted vertically and in parallel and they may be mounted as a bundle or bundles of tubes. It is preferred that the olefin feed be introduced at the top of the tubes such that it passes through the tubes in a downward direction. The tubes are contained within a reactor shell, and the temperature control fluid preferably flows vertically upwards within the reactor shell in counter current to the direction of the flow of the olefin feed.

Preferably, there are baffles provided on the shell side in order to guide the flow of the temperature control fluid. These baffles typically are arranged perpendicular to the reactor tubes. Alternatively, arrangements may comprise co-current upflow or co-current downflow. In one embodiment of the invention, the temperature control fluid may be an organic fluid such as hot oil. However, in a preferred embodiment the temperature control fluid is water, preferably, maintained at pressure in the range of 3 or 5 to 85 bar gauge which results in a boiling temperature in the range of 150° C. or 160° C. to 300° C. The temperature of the water may be controlled by varying the pressure in the steam drum that separates steam from the boiling water, provides the water for boil up on the shell side of the reactor and collects the shell side outlet stream. In this way, the peak temperature, wherever it may occur inside the reactor tube, may be controlled to be within the desired difference from the temperature of the temperature control fluid at the reactor outlet. The lowest reactor temperature which is typically the inlet temperature is preferably maintained at or above 140° C. In preferred operations, the lowest temperature in the reactor tube is kept at least at 170° C., preferably, at least at 180° C., more preferably, at least at 190° C.

In yet another embodiment, a plurality of oligomerisation reactors are placed in parallel. When the catalysts in the different reactors are not of the same age, this offers the opportunity to adapt the distribution of the total feed over the different reactors to optimize productivity in terms of conversion, temperature control, and reactor run length. This balancing of feed over a set of parallel reactors may be assisted with on-line analyses of the reactor effluents, showing individual reactor conversions, and may be performed automatically by a multi-tiered control algorithm involving time delay calculations to keep the overall process as close as possible to its optimum productivity.

The oligomerisation process is ideally carried out at a pressure which is sufficient to maintain a liquid or supercritical (also known as a dense) phase of hydrocarbon in contact with the catalyst. This liquid or supercritical hydrocarbon phase maintains conditions whereby the undesirable high molecular weight polymers or tar that are formed are more readily washed off the catalyst, thereby prolonging the catalyst life. The liquid or dense phase also is more effective in removing heat away from the active sites on the catalyst, thereby suppressing the formation of higher molecular weight polymers or tar on the catalyst during operation.

In practice, employing a regenerated zeolite catalyst, the olefin-containing feedstock is contacted with the catalyst at a temperature, pressure, and period of time which are effective to result in conversion of at least a portion of the compounds in the feed to the desired oligomer product(s). For example, the olefin to be oligomerised may be an olefin of from 3 to 9 carbon atoms, preferably from 3 to 6 carbon atoms. The contacting will generally be carried out at a temperature in the range from about 125° C. to about 300° C. It will be appreciated of course, that the optimum temperature will be a function of the specific reactants employed, their concentration in the feed and the catalyst employed. The contact temperature will typically be increased over the course of a run in order to maintain economically acceptable overall conversion.

The reactor temperature profile may be controlled by raising the temperature of the feed to the reactor. The temperature may be raised to, for example, from 150° C. to 250° C., alternatively, from 160° C. and 190° C. prior to introduction into the reactor, and this may be accomplished by the provision of any suitable heating means. In a preferred embodiment, the feed is heated by use of the heat generated in the reactor, such as by using the steam that has been generated to control the temperature in the shell side of the reactor, or by the heat contained in the reactor effluent, preferably by means of a feed effluent exchanger.

When the fresh feed is rich in olefin, control of conditions within the reactor tube may be affected by running low conversion per pass and a recycle of part of the unreacted olefins (mixed with the paraffins of the same carbon number) separated from the reactor product stream. The recycle ratio (weight of recycle on weight of fresh feed) may be controlled within a wide range, e.g., 0.1 to 2.5, preferably 0.2 to 2.0. For example, the ratio can be low, such as 0.2 or 0.3, but can also be higher, such as 0.5, 1.0, 1.5 or 2.0. Typically, the recycle ratio will be selected depending on, for example, the fresh feed composition, the availability (or lack thereof) of another suitable diluent, and any limits on the maximum concentration of olefins in the purge stream. This purge stream contains unreacted olefins, and in one arrangement typically comprises all or part of the LPG stream coming from the distillation tower that separates the unreacted olefins and paraffins from the rest of the reaction product after the reactor; such tower is usually called the stabiliser and is often in the first position.

The above-described recycle operation permits the reactor to be operated at a relatively low per-pass conversion but with a high overall conversion. This enables the overall desired product yield to be optimised, optionally to be maximised. By way of example the per-pass conversion may be as low as 50% and may be achieved by steam drum pressure reduction (in the case where the temperature control fluid is water).

By fresh feed that is rich in olefin is meant, for example, in the case of a propylene feed, a feed containing at least 70 wt %, at least 85 wt %, at least 92 wt %, or at least 97 wt % propylene. For a butenes feed is meant a feed containing at least 65 wt %, at least 80 wt %, at least 90 wt %, or at least 94 wt % butenes. Isobutylene may be present in proportions as low as 1 wt % or 0.5 wt % or less; or alternatively in higher amounts such as up to 18 wt % or up to 22 wt % based on total fresh feed.

The temperature along the reactor tube may also be controlled by filling the reactor tube with a more active catalyst in the bottom of the tube (part near the outlet) and a less active catalyst in the upper (inlet) part of the tube. Such an arrangement is disclosed in our PCT Publication No. WO 2005/118512.

The olefin feed to the reactor is generally a mixture of a reactive olefin and an unreactive diluent, which is typically an alkane, preferably having the same carbon number as the olefin. This has often required the expensive addition of diluent to an olefin containing refinery feed. Typically, the diluent may be additional amounts of the alkane found in the refinery feed and/or it may be provided by recycle of the unreacted material derived from the reactor. The need for diluent not only adds to the expense of the operation but it also reduces the volumetric yield of the reaction with associated economic debits. It is therefore desirable to reduce the amount of diluent required. The rate of heat generated by the oligomerisation reaction depends upon the concentration of the olefin in the feed. The higher the concentration of olefin, the more reactive the feed and the greater the heat that is generated.

The olefin feed may be obtained from an oxygenate stream. In this embodiment, the olefin feed stream that is oligomerised is predominantly derived from an oxygenate to olefins unit; meaning that at least 50 wt % of the olefin feed, preferably, at least 60 wt %, and more preferably, at least 70 wt % of the olefin feed is derived from an oxygenate to olefins unit. Such a feed stream should be low in sulphur, nitrogen, and chlorine to the extent that essentially no pretreatment will be required for removal of such components. In addition, such a feed stream should have a relatively low concentration of paraffins compared to such sources as olefins from cracked hydrocarbons. However, such a feed stream will generally contain at least one oxygenated hydrocarbon at a level which would likely adversely impact catalytic life of the zeolite oligomerisation catalyst. Therefore, removal of such components is likely required. The benefit in using an oxygenate to olefins stream is that lower levels of inert components, such as propane and butane, are present.

Also reactor operations may contribute to a reduction of the peak temperature. Operating at lower per pass conversions, typically combined with separating and recycling part of the unreacted molecules from downstream of the process to the reactor feed, flattens the temperature profile in the reactor. This is easier when the fresh feed to the oligomerisation process contains less inerts such as alkanes, because a high overall olefin conversion may still be obtainable for the lower per pass conversion, while the olefin concentration in the reactor feed is still conveniently high so that a high reactor volume efficiency is obtained.

It is believed that use of a feed that is dry or has a low water level enables the reactor to operate at a lower temperature than has been used with previous systems that employed a hydrated feed. In particular, the lower temperature may be used at start up of a reaction run. The ability to use a lower temperature at start up contributes to the longer catalyst life or reactor run length, because in commercial operations the reaction is allowed to continue until the temperature rises to a certain level when the reaction is stopped, as above this temperature cracking, severe coke formation and rapid catalyst deactivation occurs. Typically, the end of run temperature is from 260° C. to 300° C., preferably, 270° C. to 290° C.

Mixtures of two or more zeolites, e.g., a mixture of ZSM-22 and ZSM-57 can be used as the oligomerisation catalyst as disclosed in EP 0746538 B and the regeneration techniques are applicable to each or both catalysts.

An as-synthesized zeolite is advantageously converted to its acid form, for example by acid treatment, e.g., by HCl, or by ammonium ion exchange, and subsequently calcined before use. The calcined materials may be post-treated, such as by steaming. The zeolites might be supported or unsupported, for example in the powder form, or used as an extrudate with an appropriate binder. Where a binder is employed, the binder is conveniently a metal oxide, such as alumina or silica and is present in an amount such that the oligomerisation catalyst contains for example from 1 to 99 wt % of the zeolite, more preferably from 50 to 70 wt %.

The regenerated catalyst of this invention can be used in connection with the conversion of a mixture of $C_3$ and $C_{11}$ olefins to gasoline blending stock by oligomerisation. In such an embodiment, the feed will be comprised of at least about 25% by weight of olefins.

The regenerated catalyst may be used for the oligomerisation of olefins such as ethylene, propylene, butenes and amylenes to produce $C_6$ to $C_{14}$ olefins which can be used as feeds for hydroformylation reactions for the production of aldehydes and alcohols. The aldehydes may then be oxidised to produce acids or hydrogenated to produce alcohols. The alcohols may then be used in the production of synthetic esters such as plasticiser esters or synthetic lubricants or in the production of surfactants. The olefins may be hydroformylated using low pressure rhodium catalysed hydroformylation technology or high pressure hydroformylation technology which is typically cobalt catalysed, but rhodium is also used. The present invention is particularly useful in the production of catalysts used to produce feedstocks which are hydroformylated in the manner described in International Publication No. WO2005/058787. Where the aldehydes produced by this method are hydrogenated, this may readily be accomplished by the method described in International Publication No. WO2005/058782 that may, for example, use a cuprous chrome catalyst or a sulfided Ni/Mo catalyst.

The aldehydes may be oxidized to the corresponding carboxylic acids. Both the acids and the alcohols may be esterified to esters. These esters may be plasticizer esters for PVC, such as phthalates, adipates, trimellitates or cyclohexanoates or they may be lubricant esters or lubricant additive esters such as polyol esters. A suitable esterification process is described in WO 2005/021482 or WO 2006/125670, in which a titanium-based organometallic catalyst may be used. The oligomers may also be hydrogenated to alkanes which may be used as low sulphur, low aromatic, low pour point hydrocarbon fluids suitable in end uses such as solvents and thinners in paints, printing inks, as stove fuels, or as process fluids or carriers in polymerization processes.

EXAMPLES

The activity and selectivity of a regenerated ZSM-57 catalyst in the oligomerisation of a butene stream was determined The butene stream contained 65 wt % butenes, 10 wt % iso-butane, and 25 wt % butane and was hydrated with water. The catalyst was crushed and sieved to a particle size of 300-600 microns. The tests were performed in a small tubular reactor containing 2 grams of the catalyst with a feed space velocity of 12.5, the temperature set point was 185° C., and the feed hydrator was set at 40° C.

The catalysts were treated by heating in nitrogen for several hours and then heating in dry air under the conditions as set out in the following Table 1 which gives the $C_8$ selectivity of the oligomerisation reaction.

TABLE 1

| Catalyst | Regeneration Temperature ° C. | Regeneration Time Hrs | C$_8$ selectivity Wt % |
|---|---|---|---|
| Fresh | — | — | 75.7 |
| Treatment 1 | 400 | 48 | 75.5 |
| Treatment 2 | 500 | 48 | 75.0 |
| Treatment 3 | 600 | 48 | 70.00 |

A series of similar runs to were performed in which the water content of the air was varied.

The results were as follows:

TABLE 2

| Catalyst | Water content Vol % | Regeneration Temperature ° C. | Regeneration Time hrs | C$_8$ selectivity Wt % |
|---|---|---|---|---|
| Fresh | — | — | — | 75.5 |
| Treatment 1 | Dry | 400 | 48 | 75.5 |
| Treatment 2 | 3.2 | 400 | 48 | 73.5 |
| Treatment 3 | Steam | 400 | 48 | 68.0 |

The results show how selectivity is maintained if the temperature in the second step of treatment is no higher than 500° C. and the air that is used in the second step is dry.

What is claimed is:

1. A process for the regeneration of a catalyst selected from ZSM-22; ZSM-57, or mixtures thereof wherein the catalyst has been used for oligomerizing a C$_4$ stream to produce a product comprising octane, the process comprising the following steps:
   i) heating the catalyst to a temperature in the range from 300° C. to 450° C. under an inert dry atmosphere; and
   ii) heating the catalyst to a temperature in the range from 450° C. to 500° C. in a dry oxygen-containing atmosphere to produce a regenerated catalyst;
wherein the regenerated catalyst has an octane selectivity of at least 75 wt %.

2. The process according to claim 1 in which the total time for regeneration is no more than 100 hours.

3. The process according to claim 1 in which the second step is performed in less than 68 hours.

4. The process according to claim 1 in which the inert atmosphere employed in the first step is a nitrogen atmosphere.

5. The process according to claim 1 in which the dry oxygen containing atmosphere employed in the second step is air having a dew point of −10° C. or below.

* * * * *